US012350186B2

(12) United States Patent
Paik et al.

(10) Patent No.: US 12,350,186 B2
(45) Date of Patent: Jul. 8, 2025

(54) NON-FIXED SHOULDER BRACE

(71) Applicants: SEOUL NATIONAL UNIVERSITY R&DB FOUNDATION, Seoul (KR); SEOUL NATIONAL UNIVERSITY HOSPITAL, Seoul (KR)

(72) Inventors: Nam-Jong Paik, Seoul (KR); Jihong Park, Seoul (KR); Jae-Young Lim, Seoul (KR); Won-Seok Kim, Seoul (KR); Yong-Lae Park, Seoul (KR); Junghan Kwon, Seoul (KR)

(73) Assignees: SEOUL NATIONAL UNIVERSITY R&DB FOUNDATION, Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 751 days.

(21) Appl. No.: 17/622,925

(22) PCT Filed: Jun. 26, 2020

(86) PCT No.: PCT/KR2020/008395
§ 371 (c)(1),
(2) Date: Jul. 25, 2022

(87) PCT Pub. No.: WO2020/263033
PCT Pub. Date: Dec. 30, 2020

(65) Prior Publication Data
US 2022/0387208 A1 Dec. 8, 2022

(30) Foreign Application Priority Data

Jun. 28, 2019 (KR) .................. 10-2019-0077651
Jun. 28, 2019 (KR) .................. 10-2019-0078149

(51) Int. Cl.
*A61F 5/37* (2006.01)
*A61B 5/11* (2006.01)
(Continued)

(52) U.S. Cl.
CPC ............ *A61F 5/3738* (2013.01); *A61B 5/112* (2013.01); *A61B 5/1126* (2013.01);
(Continued)

(58) Field of Classification Search
CPC ............ A61F 5/01–0104; A61F 5/0118; A61F 5/013; A61F 5/37; A61F 5/3715;
(Continued)

(56) References Cited

U.S. PATENT DOCUMENTS 3,892,230 A 7/1975 Baker et al.
4,198,964 A * 4/1980 Honneffer ............. A61F 5/3738
602/19

(Continued)

FOREIGN PATENT DOCUMENTS

GB 2467974 A 8/2010
JP 2002-177310 6/2002
(Continued)

OTHER PUBLICATIONS

Extended European Search Report, Application No. 20831108.4, Mailed Jun. 6, 2023 (9 pages).

*Primary Examiner* — Michelle J Lee
(74) *Attorney, Agent, or Firm* — Ware, Fressola, Maguire & Barber LLP

(57) ABSTRACT

A non-fixed shoulder brace is provided comprising: an affected shoulder support which is supported on an affected shoulder of a wearer; a waist support coupled to the wearer's waist; an affected arm mounting part in which the wearer's affected arm is inserted and which is supported by means of an affected shoulder strap member from the affected shoulder support; and an affected upper limb exercise assistance apparatus coupled to both ends of the waist support and disposed between the wearer's waist and the affected arm mounting part.

7 Claims, 14 Drawing Sheets

(51) Int. Cl.
  *A61F 5/01* (2006.01)
  *A61N 1/04* (2006.01)
  *A61N 1/36* (2006.01)

(52) U.S. Cl.
  CPC ............ *A61F 5/0118* (2013.01); *A61F 5/373* (2013.01); *A61N 1/0452* (2013.01); *A61N 1/0484* (2013.01); *A61N 1/36003* (2013.01); *A61N 1/36031* (2017.08); *A61F 2005/0172* (2013.01)

(58) Field of Classification Search
  CPC ...... A61F 5/3723; A61F 5/373; A61F 5/3738; A61F 5/3753; A61F 5/3761; A61F 2005/0132; A61F 2005/0172; A61F 2005/0174; A63B 23/00; A63B 23/035; A63B 23/03516; A63B 23/12; A63B 23/1245; A63B 23/1263; A61N 1/04; A61N 1/0404; A61N 1/0408; A61N 1/0452; A61N 1/0484; A61N 1/36; A61N 1/36003; A61N 1/36014; A61N 1/3603; A61N 1/36031; A61B 5/103; A61B 5/11; A61B 5/112; A61B 5/1126
  See application file for complete search history.

(56) References Cited

U.S. PATENT DOCUMENTS

| | | | |
|---|---|---|---|
| 4,441,707 A * | 4/1984 | Bosch | ................ A63B 23/1209 482/131 |
| 5,188,587 A | 2/1993 | McGuire et al. | |
| 5,203,763 A | 4/1993 | Lajiness-O'Neill | |
| 5,590,420 A * | 1/1997 | Gunn | .................... A41D 31/12 2/243.1 |
| 8,016,780 B1 | 9/2011 | Sickles | |
| 2006/0211956 A1* | 9/2006 | Sankai | ................. A61F 5/0102 601/5 |
| 2010/0160842 A1* | 6/2010 | Wickstrom | ........... A61F 5/3738 602/4 |
| 2012/0101419 A1 | 4/2012 | Bonutti et al. | |
| 2016/0000635 A1 | 1/2016 | Miyake | |
| 2018/0028274 A1 | 2/2018 | Doyle | |
| 2018/0116893 A1 | 5/2018 | Lebolt et al. | |
| 2020/0038218 A1* | 2/2020 | Ingvast | ............... A61B 5/1071 |

FOREIGN PATENT DOCUMENTS

| | | | |
|---|---|---|---|
| JP | 2012011102 A | | 1/2012 |
| JP | 2014-128464 | | 7/2014 |
| KR | 10-0883324 B1 | | 2/2009 |
| KR | 10-2010-0097070 | | 9/2010 |
| KR | 20-0465621 Y1 | | 3/2013 |
| KR | 10-2015-0120084 | | 10/2015 |
| KR | 20150120084 A | * | 10/2015 |
| KR | 10-1861041 B1 | | 5/2018 |
| KR | 10-2019-0065271 | | 6/2019 |
| KR | 20190124651 A | * | 11/2019 |
| WO | 2018065459 A1 | | 4/2018 |

* cited by examiner (a)

(b)

(a)

(b)

NON-FIXED SHOULDER BRACE

TECHNICAL FIELD

The present application relates to a non-fixed shoulder brace and, more particularly, to a shoulder brace that may prevent contracture of shoulder joint and elbow joint of an affected shoulder by inducing movement of an affected arm through an affected upper limb exercise assistance apparatus.

NATIONAL R&D PROJECT FOR SUPPORTING INVENTION

Subject No.: 2016R1A5A1938472
Name of Department: Ministry of Science and ICT
R&D Agency: National Research Foundation of Korea
Project Name: Basic Research Program Advanced Research Center Support Program (ERC) by Ministry of Science and ICT
Subject Name: Center for SoFT meta-Human
Contribution Ratio: 1/1
Management Agency: Seoul National University SNU R&DB Foundation
Research Period: Dec. 11, 2016-Dec. 31, 2022

BACKGROUND ART

Recovery of shoulder function after cerebral apoplexy is a precondition for using hands and is important for walking and performing daily activities.

As shown in FIG. 10, 81% of patients with cerebral apoplexy have subluxation of affected shoulder joint due to hemiplegia, and a prevalence of pain in a shoulder joint is 42 to 73%.

In order to prevent this situation, a fixed-type brace as shown in FIG. 11 is generally clinically used at present for most patients with hemiplegia.

However, although it is important to prevent subluxation of a shoulder joint through a shoulder brace, there is a problem that contracture of the shoulder joint and elbow joint is caused and the contracture not only interferes with recovery of upper limb function but also causes pain in the shoulder joint.

For example, as shown in FIG. 12, a shoulder brace 100 having an arm support 200 adjusts the abduction angle of a shoulder through a shoulder support 400 and an arm protector 300, but it also causes contracture of the shoulder joint and elbow joint, which interferes with recovery of the function of the upper arm and causes pain in the shoulder joint.

Accordingly, it is difficult to achieve both of two contradictory treatment targets of preventing subluxation of a shoulder joint as well as of reducing contracture and pain of the shoulder joint and elbow joint using an existing fixed-type shoulder joint brace, so there is a need for a new type of brace.

PRIOR ART LITERATURE

Patent Literature

1. Korean Patent No. 0883324

SUMMARY OF THE DISCLOSURE

In order to solve the problems of the related art described above, an objective of the present invention is to provide a shoulder brace that allows for movement of an affected arm.

In an aspect of the present application, provided is a shoulder brace that can maximize the rehabilitation effect of a wearer and also prevent contracture of joints by measuring movement of a normal arm according to walking of the wearer and inducing a corresponding movement of an affected arm.

In another aspect of the present application, provided is a shoulder brace that can maximize the rehabilitation effect of a wearer and prevent contracture of joints by maintaining a pivot motion of a normal arm while preventing subluxation of an affected arm joint.

According to an aspect, in order to achieve the objectives, in exemplary embodiments of the present application, a non-fixed shoulder brace of the present application includes: an affected shoulder support which is supported on an affected shoulder of a wearer; a waist support coupled to the wearer's waist; an affected arm mounting part in which an arm of an affected upper limb of the wearer is inserted and that is supported by an affected shoulder strap member from the affected shoulder support; and an affected upper limb exercise assistance apparatus coupled to both ends of the waist support and disposed between the wearer's waist and the affected arm mounting part, in which the affected upper limb exercise assistance apparatus assists movement of the affected arm mounting part.

In an embodiment, the affected upper limb exercise assistance apparatus of the present application may include: a first cable connected to a front of the affected arm mounting part; a second cable connected to a rear of the affected arm mounting part; a motor unit having the first cable and the second cable wound thereon and tensioning the first cable and the second cable; a control unit controlling driving force and rotation direction of the motor unit; and a power unit supplying power to the motor unit and the control unit.

In an embodiment, the affected upper limb exercise assistance apparatus may be manufactured to have a type of moving an affected arm of a wearer by pulling a cable using an electric motor and a type of using pneumatic artificial muscles.

In an embodiment, the non-fixed shoulder brace of the present application may further include a normal arm mounting part in which an arm of the wearer's normal upper limb is inserted, in which the normal arm mounting part may include a first inertia sensor, and the control unit may extract a walk cycle of a wearer from a signal received from the first inertia sensor and may correct the driving force and the rotation direction of the motor unit in accordance with the walk cycle.

In an embodiment, the affected arm mounting part of the present application may include: a tension sensor and a second inertia sensor that measure a degree of subluxation of an affected upper limb; and an electric stimulator that applies electrical stimulation to muscles of the affected upper limb in accordance with the walk cycle of the wearer and the degree of subluxation of the affected arm.

In an embodiment, the waist support and the affected shoulder support of the present application may be connected through a plurality of suspending shoulder strap members.

In an embodiment, the affected upper limb exercise assistance apparatus of the present application may include an elastic support disposed to face the waist of the wearer.

In an embodiment, the affected upper limb exercise assistance apparatus of the present application may include a first friction reduction pad disposed to face the affected arm mounting part, and the affected arm mounting part may include a second friction reduction pad disposed to face the waist of the wearer.

In an embodiment, the first and second friction reduction pads may be made of Teflon.

According to another aspect, in order to achieve the objectives, in exemplary embodiments of the present application, a non-fixed shoulder brace of the present application includes: an affected shoulder support which is supported on an affected shoulder of a wearer; a waist support coupled to the waist of the wearer; an affected arm mounting part in which an arm of an affected upper limb of the wearer is inserted and that is supported by an affected shoulder strap member from the affected shoulder support; a normal arm mounting part in which an arm of a normal upper limb of the wearer is inserted; and an affected upper limb exercise assistance apparatus coupled to both ends of the waist support and disposed between the waist of the wearer and the affected arm mounting part.

In an embodiment, the affected upper limb exercise assistance apparatus may include a belt connecting the affected arm mounting part and the normal arm mounting part and a plurality of belt insertion holes through which the belt is inserted.

In an embodiment, the waist support and the affected shoulder support of the present application may be connected through a plurality of suspending shoulder strap members.

In an embodiment, the affected upper limb exercise assistance apparatus of the present application may include an elastic support disposed to face the waist of the wearer.

In an embodiment, the affected upper limb exercise assistance apparatus of the present application may include a first friction reduction pad disposed to face the affected arm mounting part, and the affected arm mounting part may include a second friction reduction pad disposed to face the waist of the wearer.

In an embodiment, an inner side of the affected upper limb exercise assistance apparatus of the present application may be formed to be fitted to the curve of the waist of the wearer, and the upper half of the upper side thereof may be narrow and curved in comparison to the lower half to be fitted to the curve of the armpit of the wearer.

In an embodiment, the outer side of the affected upper limb exercise assistance apparatus of the present application may be made of a hard material for inducing movement of the affected arm of the wearer when the wearer walks.

In an embodiment, the first and second friction reduction pads may be made of Teflon.

In an embodiment, the affected upper limb exercise assistance apparatus may assist a wearer to move forward the normal arm mounting part by pivoting forward the normal arm and may assist the affected arm mounting part to pivot rearward the affected arm of the wearer in response to movement of the normal arm mounting part.

According to the present invention, it is possible to prevent subluxation of the affected shoulder joint while reducing contracture and pain by inducing movement of the affected arm from movement of a normal arm.

DESCRIPTION OF REFERENCE NUMBERS

Figure 1A:
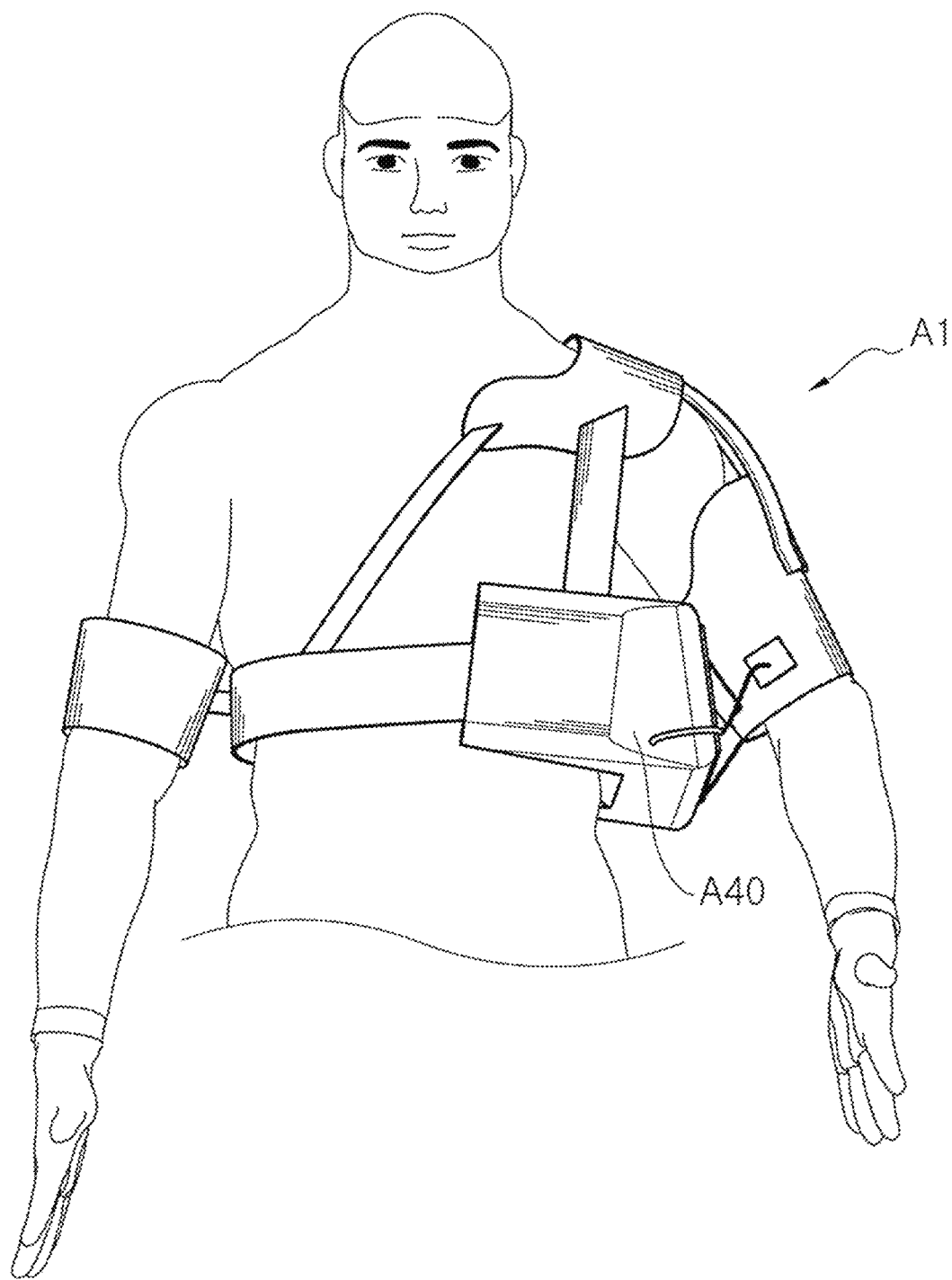
FIGS. 1A and 1B are perspective views schematically showing a front and a back of a user wearing a non-fixed shoulder brace according to a first embodiment of the present application.

A1: non-fixed shoulder brace A11: affected shoulder support
A11a: tension sensor A12: suspending shoulder strap member
A13: waist support A14: apparatus support
A15: affected shoulder strap
A21: affected arm mounting part A22a: second inertia sensor
A22: electric stimulator A23: second friction reduction pad
A32: first inertia sensor A40: affected arm assistant
A41: elastic support A42a: first cable
A42b: second cable A43: first friction reduction pad
A44: motor unit A45: control unit
A46: power unit
P1: non-fixed shoulder brace P11: affected shoulder support
P12: suspending shoulder strap member P13: waist support
P15: affected shoulder strap
P21: affected arm mounting part
P22: affected arm mounting part connection portion
P23: second friction reduction pad P31: normal arm mounting part
P32: normal arm mounting part connection portion
P40: affected upper limb exercise assistance apparatus
P41: belt P42: belt insertion hole
P43: first friction reduction pad P45: elastic support

DETAILED DESCRIPTION

Hereafter, a non-fixed shoulder brace according to an embodiment of the present application is described through preferred embodiments of the present application with reference to the accompanying drawings.

In various embodiments, components having the same configuration are given the same reference numerals and are representatively described in an embodiment, and only different components are described in other embodiments.

Figure 1B:
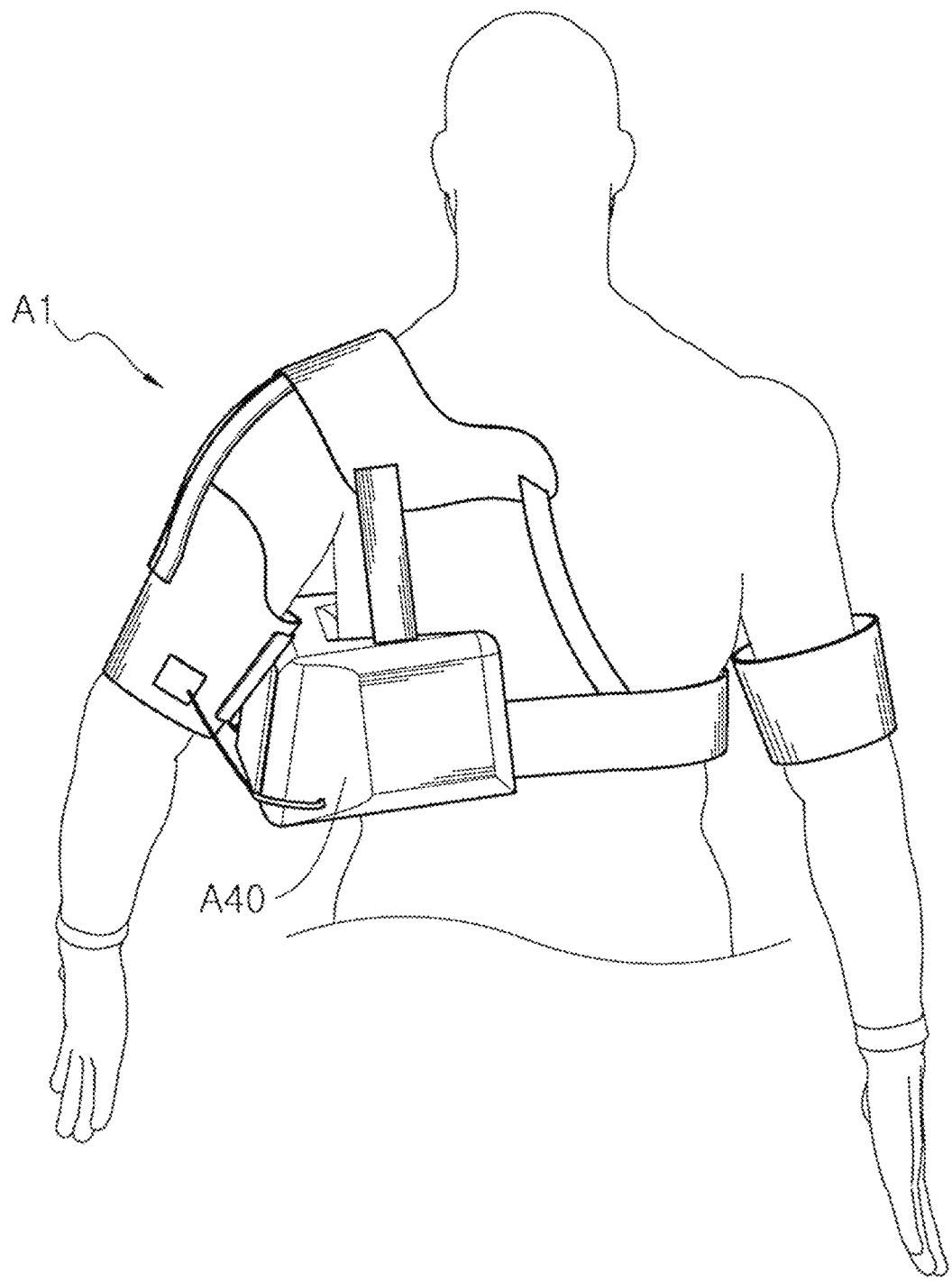

FIGS. 1A and 1B are perspective views schematically showing a front and a back of a user wearing a non-fixed shoulder brace A1 according to a first embodiment of the present application.

As shown in FIGS. 1A and 1B, a non-fixed shoulder brace A1 according to a first embodiment of the present application is designed to be worn on the upper body of a wearer; particularly, an affected upper limb exercise assistance apparatus A40 is held on a waist of the wearer by a waist support A13 and positioned between the wearer's waist and affected arm. Here the detailed components of the affected upper limb exercise assistance apparatus A40 will be described below.

Figure 2:
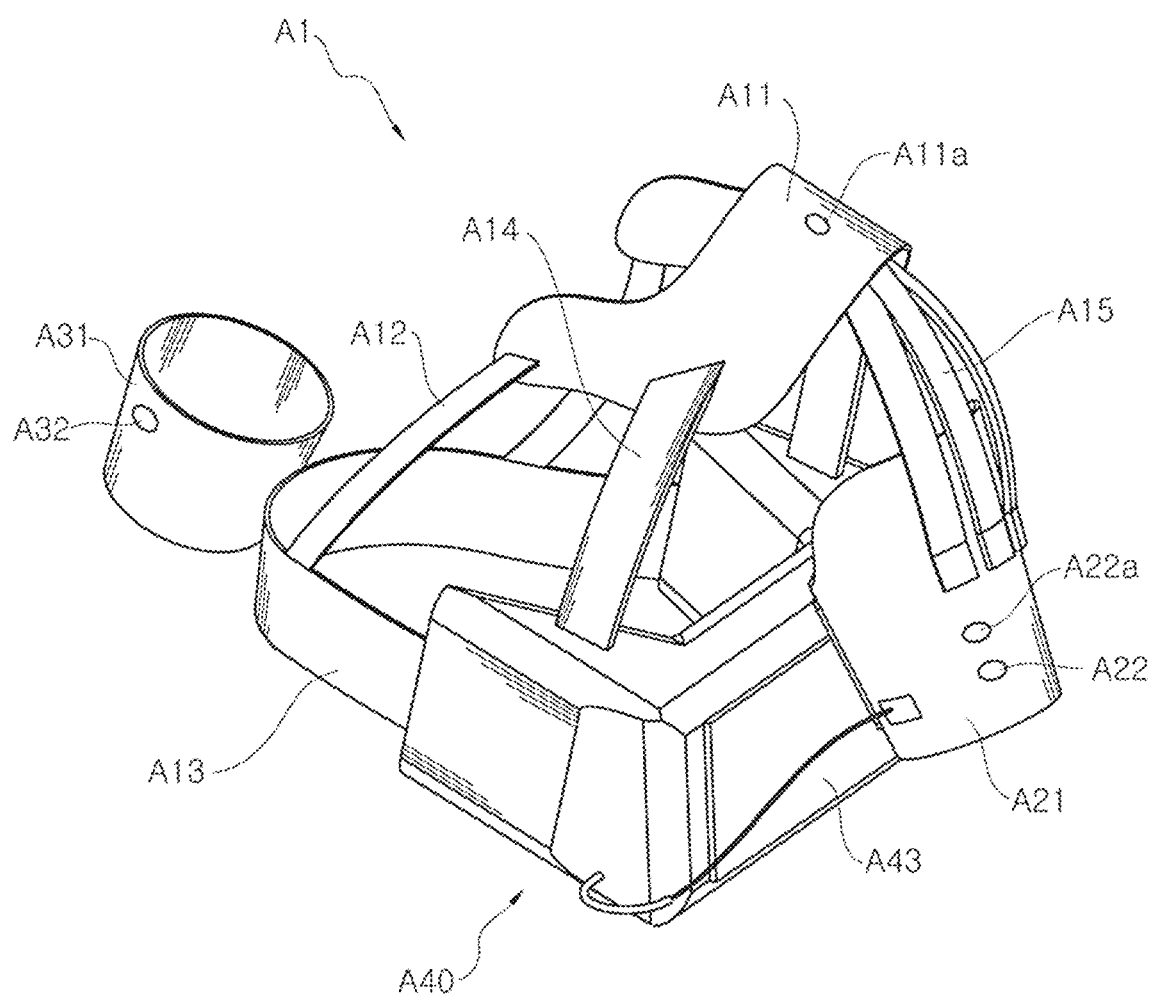
FIG. 2 is a perspective view schematically showing components of the non-fixed shoulder brace according to the first embodiment of the present application.

FIG. 2 is a perspective view schematically showing components of the non-fixed shoulder brace A1 according to the first embodiment of the present application.

As shown in FIG. 2, the non-fixed shoulder brace A1 according to the first embodiment of the present application includes an affected shoulder support A11, a waist support A13, an affected arm mounting part A21, and an affected upper limb exercise assistance apparatus A40.

In detail, the affected shoulder support A11 is supported on an affected shoulder of a wearer and the waist support A13 is coupled to the wearer's waist.

The affected arm mounting part A21 is coupled together with an arm of an affected upper limb of the wearer with the arm of the affected upper limb inserted therein.

In particular, the affected shoulder support A11 and the affected arm mounting part A21 are connected through an affected shoulder strap A15 and the affected arm mounting part A21 is pulled towards inside the wearer's shoulder, whereby it is possible to prevent dislocation of the wearer's affected shoulder.

The waist support A13 and the affected shoulder support A11 are connected through a plurality of suspending shoulder strap members A12, so it is possible to reduce a load of the affected arm, which is applied to the affected shoulder support A11, to the waist support A13.

The affected arm assistant A40 may reduce its load through an apparatus support A14.

Figure 3:
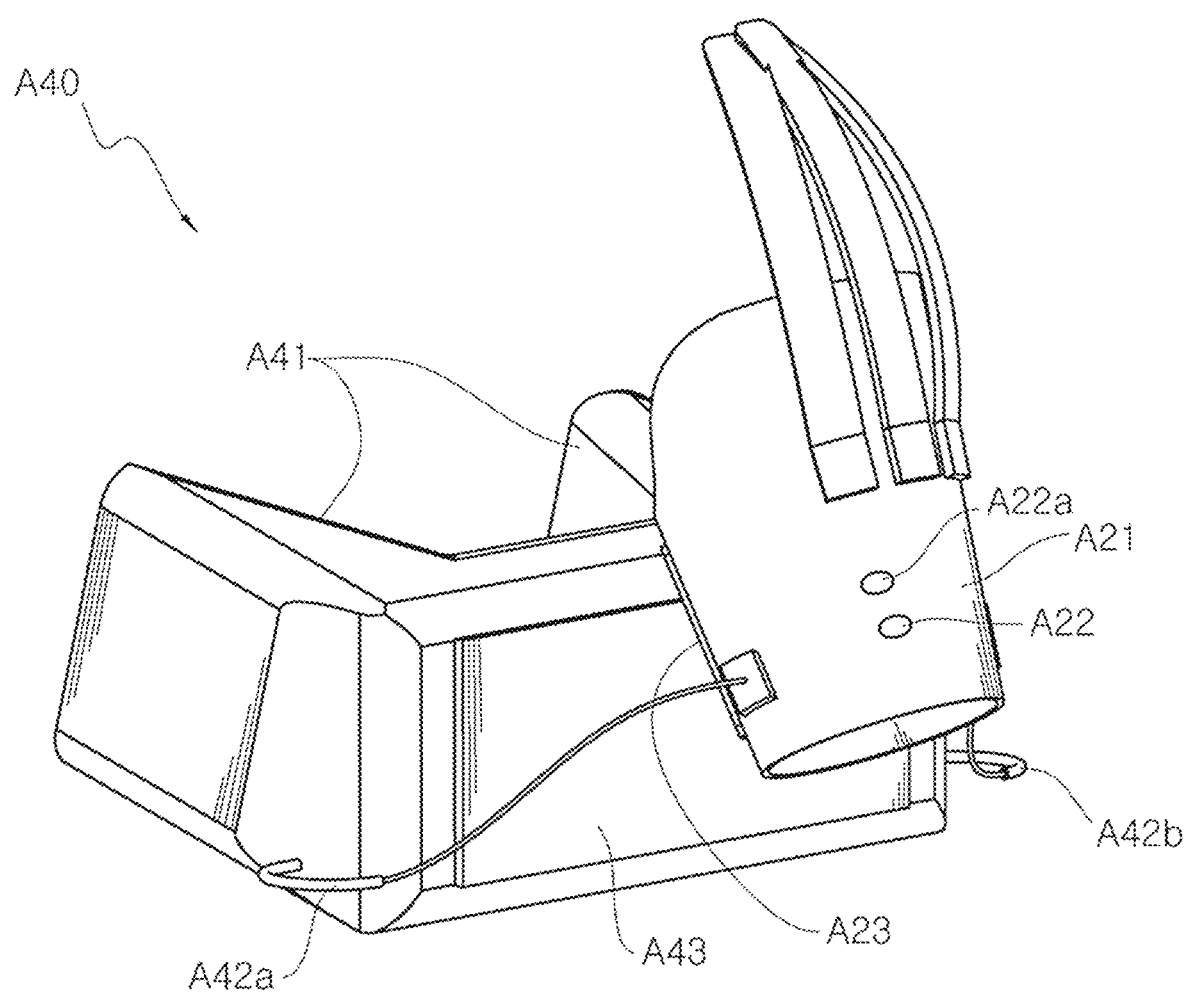
FIG. 3 is a perspective view schematically showing connection relationships between components of an affected upper limb exercise assistance apparatus and an affected arm mounting part according to the first embodiment of the present application.

FIG. 3 is a perspective view schematically showing connection relationships between components of an affected upper limb exercise assistance apparatus A40 and an affected arm mounting part A21 according to the first embodiment of the present invention.

As shown in FIG. 3, the affected upper limb exercise assistance apparatus A40 is coupled to the affected arm mounting part through a first cable A42a connected to a front of the affected arm mounting part A21 and a second cable A42b connected to a rear of the affected arm mounting part A21.

The affected upper limb exercise assistance apparatus A40 may be coupled to both ends of the waist support A13 and held on the wearer's waist.

In detail, a curved groove is formed on a side of the affected upper limb exercise assistance apparatus so that it may be easily fitted to the wearer's waist, and a portion where the curved groove is formed is made by an elastic support A41 so that a shape of the affected upper limb exercise assistance apparatus A40 may be easily deformed to be fitted to a waist shape of the wearer.

As shown in FIGS. 2 and 3, the affected upper limb exercise assistance apparatus A40 includes a first friction reduction pad A43 disposed on a side thereof facing the affected arm mounting part A21. The affected arm mounting part A21 also has a second friction reduction pad A23 disposed on a side thereof facing the wearer's waist.

Accordingly, friction between the affected arm mounting part A21 and the affected upper limb exercise assistance apparatus A40 may be reduced while the wearer's affected arm is moved, so it is possible to reduce resistance that interferes with movement of the affected arm mounting part A21 by the wearer.

In particular, the first friction reduction pad A43 and the second friction reduction pad A23 are made of Teflon, whereby friction can be minimized.

The normal arm mounting part A31 includes a first inertia sensor A32, and a program of a control unit A45 included in the affected upper limb exercise assistance apparatus A40 may extract a walk cycle of the wearer from a signal received from the first inertia sensor A32.

As shown in FIGS. 2 and 3, the non-fixed shoulder brace A1 that is the first embodiment of the present invention may improve mobility of an affected arm through electric stimulation by measuring subluxation degree of the wearer.

In detail, the affected shoulder support A11 may include a tension sensor A11a and the affected arm mounting part A21 may include a second inertia sensor A22a. Signals extracted from the tension sensor A11a and the second inertia sensor A22a may extract information about the walk cycle and the subluxation degree of the wearer from the program of the control unit A45 included in the affected upper limb exercise assistance apparatus A40. This information signal applies an electrical signal to an electric stimulator A22 of the affected arm mounting part A21 worn on an affected upper limb of the wearer, whereby electric stimulation may be applied to muscles of the wearer's affected upper limb.

Figure 4:
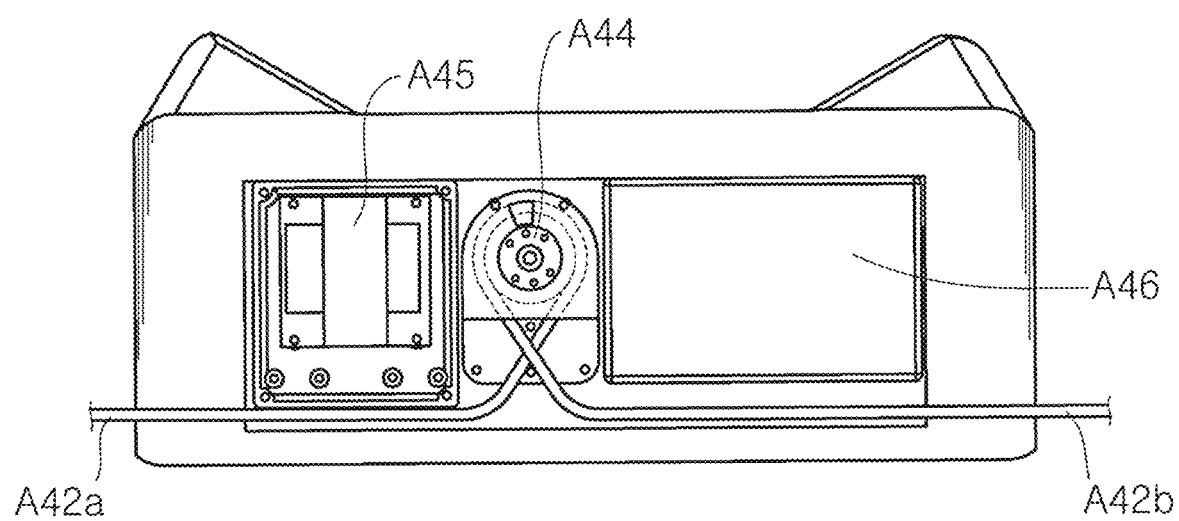
FIG. 4 is a cross-sectional view schematically showing an inside of the affected upper limb exercise assistance apparatus according to the first embodiment of the present application.

FIG. 4 is a cross-sectional view schematically showing an inside of the affected upper limb exercise assistance apparatus A40 according to the first embodiment of the present invention.

As shown in FIG. 4, the affected upper limb exercise assistance apparatus A40 includes a motor unit A44 on which the first cable A42a and the second cable A42b are wound, a control unit A45 that may control driving force and rotation direction of the motor unit A44, and a power unit A46 that supplies power to the motor unit A44 and the control unit A45.

In particular, the first cable A42a and the second cable A42b may be tensioned toward the motor unit A44 in accordance with the driving force applied to the motor unit A44. That is, when the first cable A42a is wound to be tensioned, the second cable A42b is unwound from the motor unit 44. Further, when the second cable A42b is wound to be tensioned, the first cable A42a is unwound from the motor unit A44.

Accordingly, since one motor unit A44 is driven in two directions and the first cable A42a and the second cable A42b may be separately tensioned, it is possible to simplify a design of the affected upper limb exercise assistance apparatus A40 and as well remarkably reduce space for the entire affected upper limb exercise assistance apparatus A40.

Further, the control unit A45 may control the driving force and rotation direction of the motor unit A44 and may correct the driving force and rotation direction of the motor unit A44 in accordance with the walk cycle of the wearer extracted from a signal from the first inertia sensor A32.

Further, the control unit A45 may also include a program that may control the intensity and cycle of electric stimulation that is applied to the electric stimulator A22 on the basis of the information about the walk cycle and the subluxation degree of the wearer extracted from the tension sensor A11a and the second inertia sensor A22a.

As for the power unit A46 that supplies power to the motor unit A44 and the control unit A45, for example, a chargeable battery may be used, and the affected upper limb exercise assistance apparatus A40 may be operated by a battery without being connected to an external power, so portability of the shoulder brace may be considerably improved.

Figure 5:
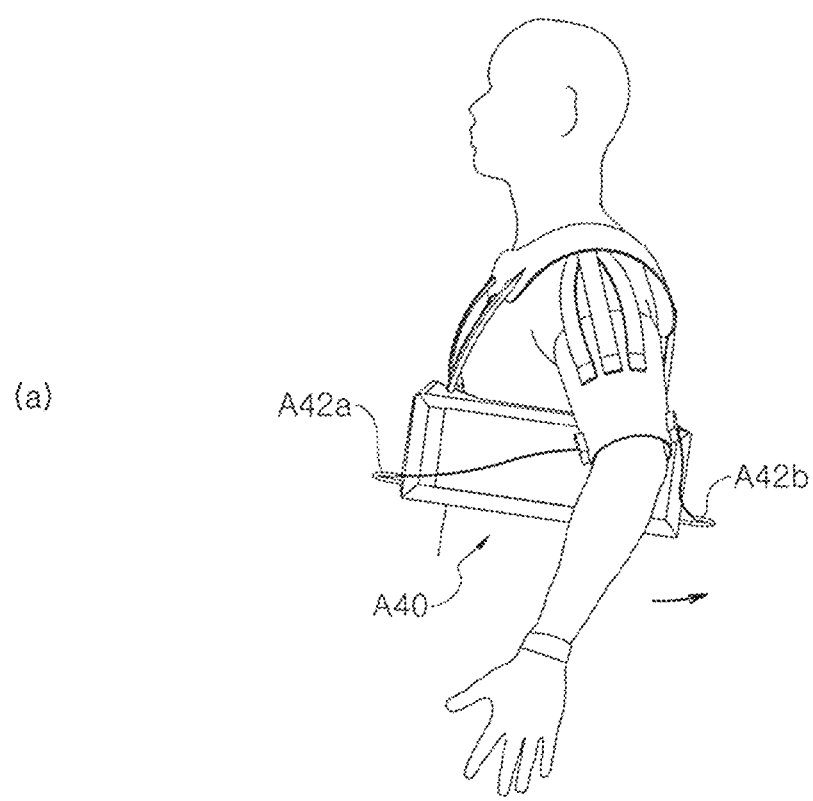
FIG. 5 is a view schematically showing movement of an affected arm of a user wearing the non-fixed shoulder brace according to the first embodiment of the present application.
Figure 5:
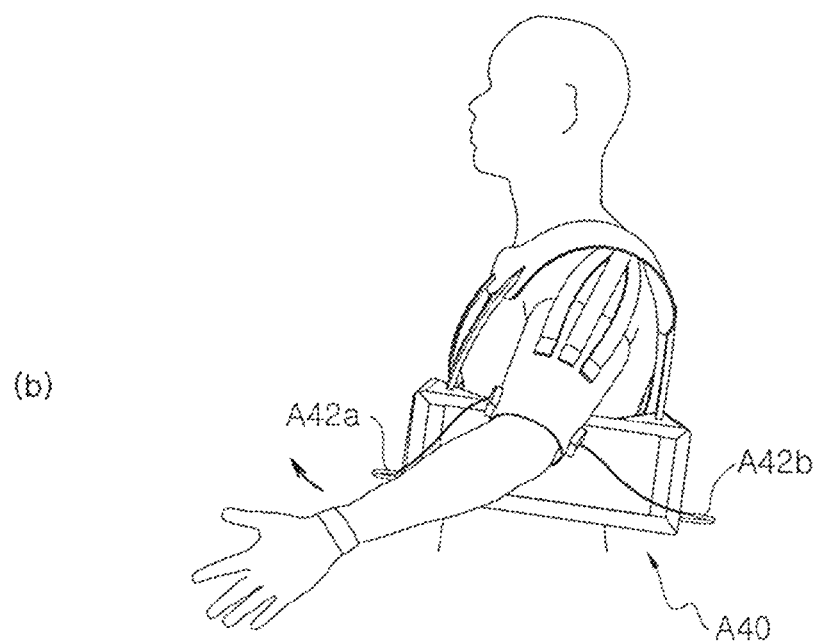

FIG. 5 is a view schematically showing movement of an affected arm of a user wearing the non-fixed shoulder brace A1 according to the first embodiment of the present invention. As described above, the first cable A42a and the second cable A42b that are tensioned in opposite directions are connected to the affected arm mounting part A21, so an affected arm of the wearer may be moved forward or backward by moving any one of the cables.

In detail, as shown in (a) of FIG. 5, when the timing at which the wearer moves rearward an affected arm in accordance with the walk cycle is reached, the motor unit A44 is driven in response thereto so that the second cable A42b tensions the affected arm mounting part A21, whereby the affected arm is moved rearward.

Further, as shown in (b) of FIG. 5, when the timing at which the wearer moves forward an affected arm in accordance with the walk cycle is reached, the motor unit A44 is driven in response thereto so that the first cable A42a tensions the affected arm mounting part A21, whereby the affected arm is moved forward.

Accordingly, since the affected upper limb exercise assistance apparatus A40 may automatically assist an affected arm to move forward and rearward in accordance with the walk cycle of the wearer, it is possible to prevent pain due to contracture of the affected shoulder joint and elbow joint of the wearer.

Figure 6A:
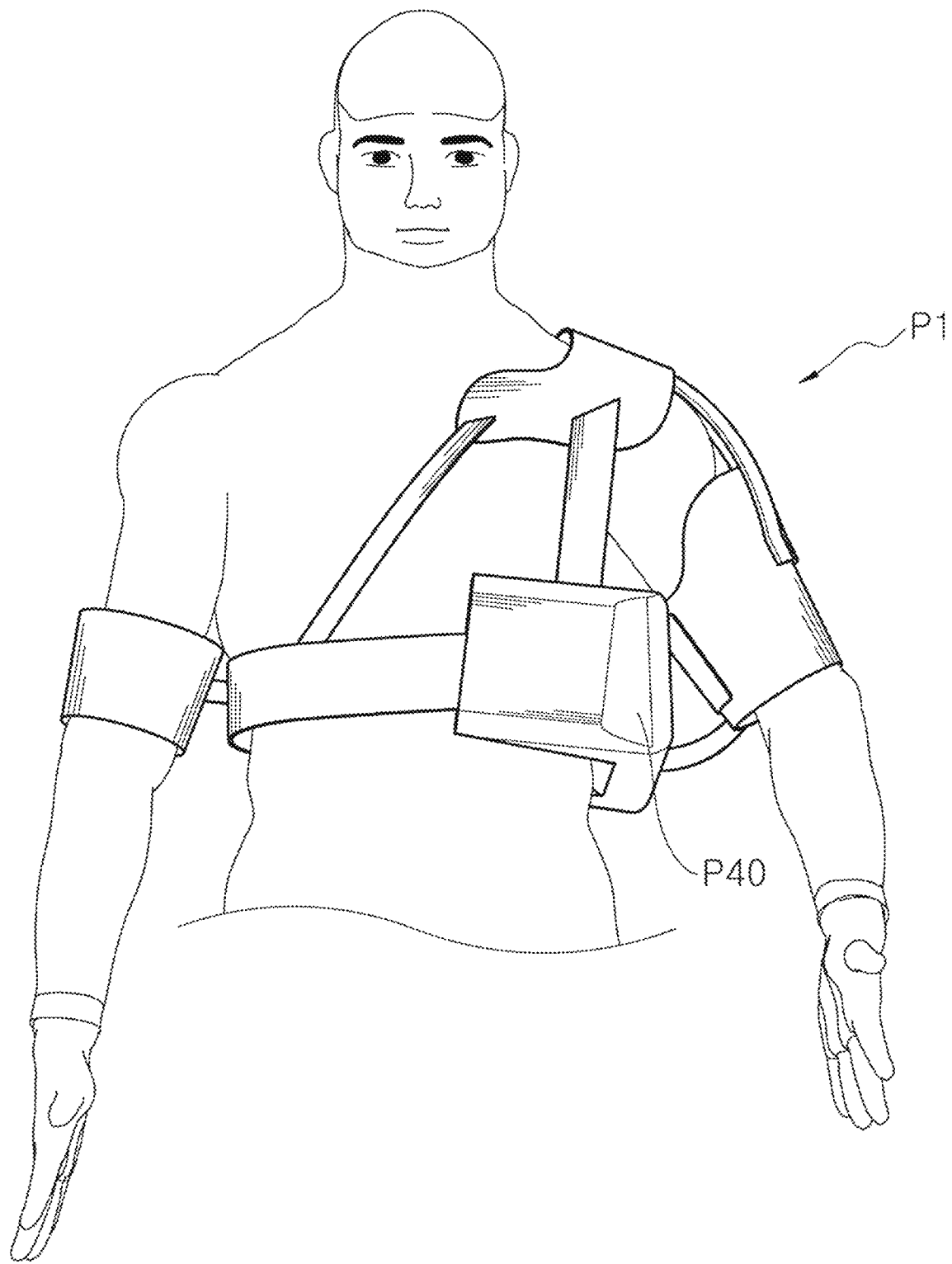
FIGS. 6A and 6B are perspective views schematically showing a front and a back of a user wearing a non-fixed shoulder brace according to a second embodiment of the present application.
Figure 6B:
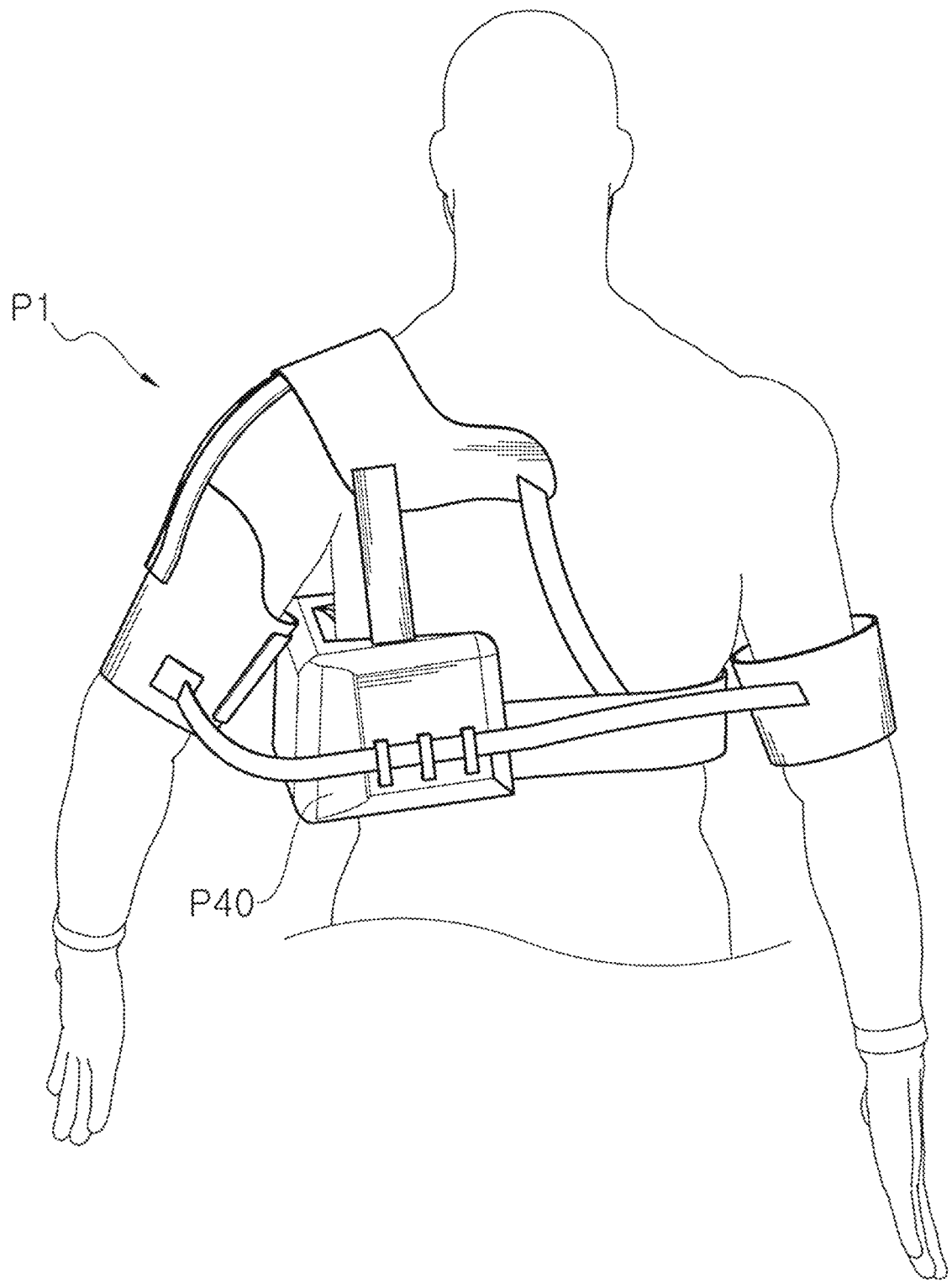

FIGS. 6A and 6B are perspective views schematically showing a front and a back of a user wearing a non-fixed shoulder brace P1 according to a second embodiment of the present invention.

As shown in FIGS. 6A and 6B, a non-fixed shoulder brace P1 according to the second embodiment of the present invention is designed to be worn on an upper body of a wearer; particularly, an affected upper limb exercise assistance apparatus P40 is held on the wearer's waist by a waist support P13 and positioned between the wearer's waist and affected arm.

The detailed components of the affected upper limb exercise assistance apparatus P40 will be described below.

Figure 7:
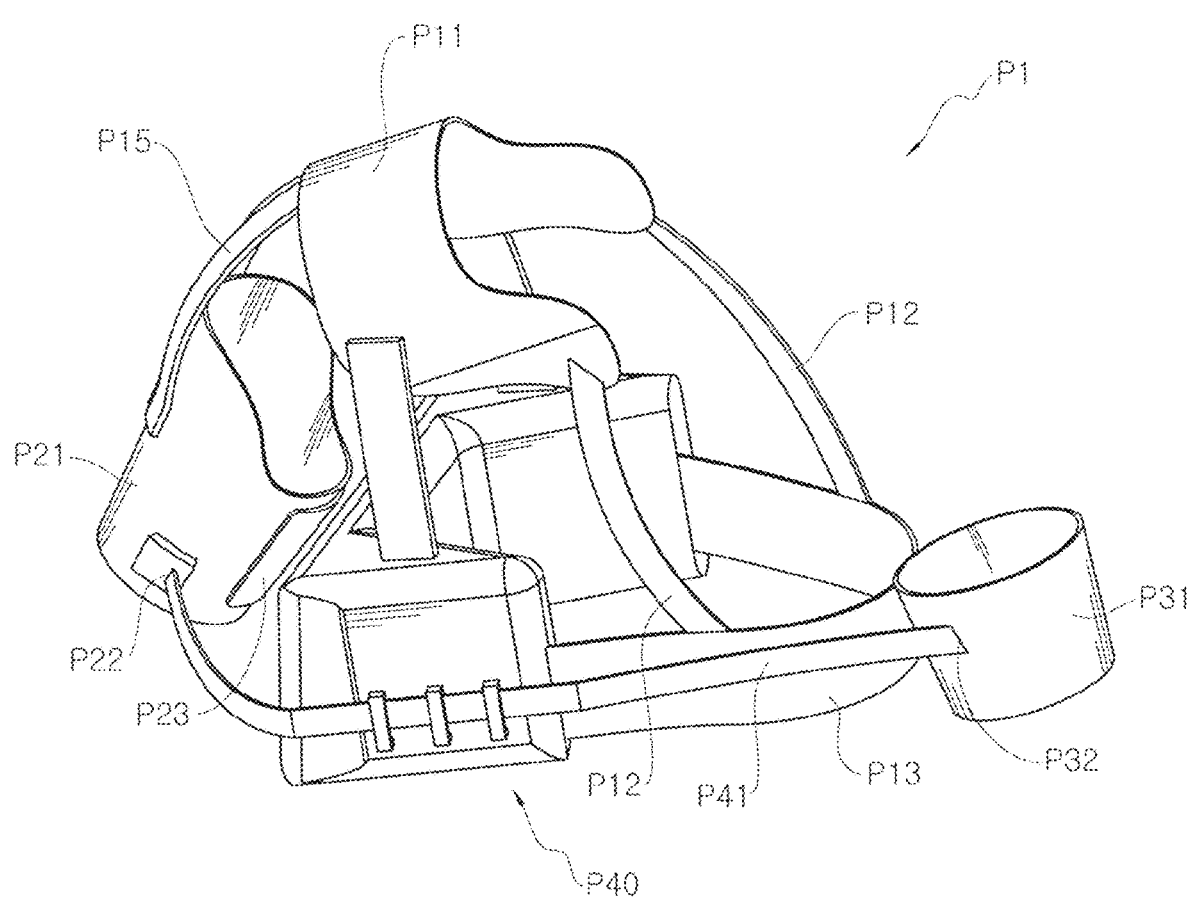
FIG. 7 is a perspective view schematically showing components of the non-fixed shoulder brace according to the second embodiment of the present application.

FIG. 7 is a perspective view schematically showing components of the non-fixed shoulder brace P1 according to the second embodiment of the present invention.

As shown in FIG. 7, the non-fixed shoulder brace P1 according to the second embodiment of the present invention includes an affected shoulder support P11, a waist support P13, an affected arm mounting part P21, a normal arm mounting part P31, and an affected upper limb exercise assistance apparatus P40.

In detail, the affected shoulder support P11 is supported on an affected shoulder of the wearer, and the waist support P13 is coupled to the wearer's waist.

The affected arm mounting part P21 and the normal arm mounting part P31 are coupled together with an arm of the affected upper limb and an arm of the normal upper limb with the arms inserted therein, respectively.

In particular, the affected shoulder support P11 and the affected arm mounting part P21 are connected through an affected shoulder strap P15 and the affected arm mounting part P21 is pulled towards inside the wearer's shoulder, whereby it is possible to prevent dislocation of the wearer's affected shoulder.

Further, the waist support P13 and the affected shoulder support P11 are connected through a plurality of suspending shoulder strap members P12, so it is possible to reduce a load of the affected arm, which is applied to the affected shoulder support P11, to the waist support P13.

Figure 8:
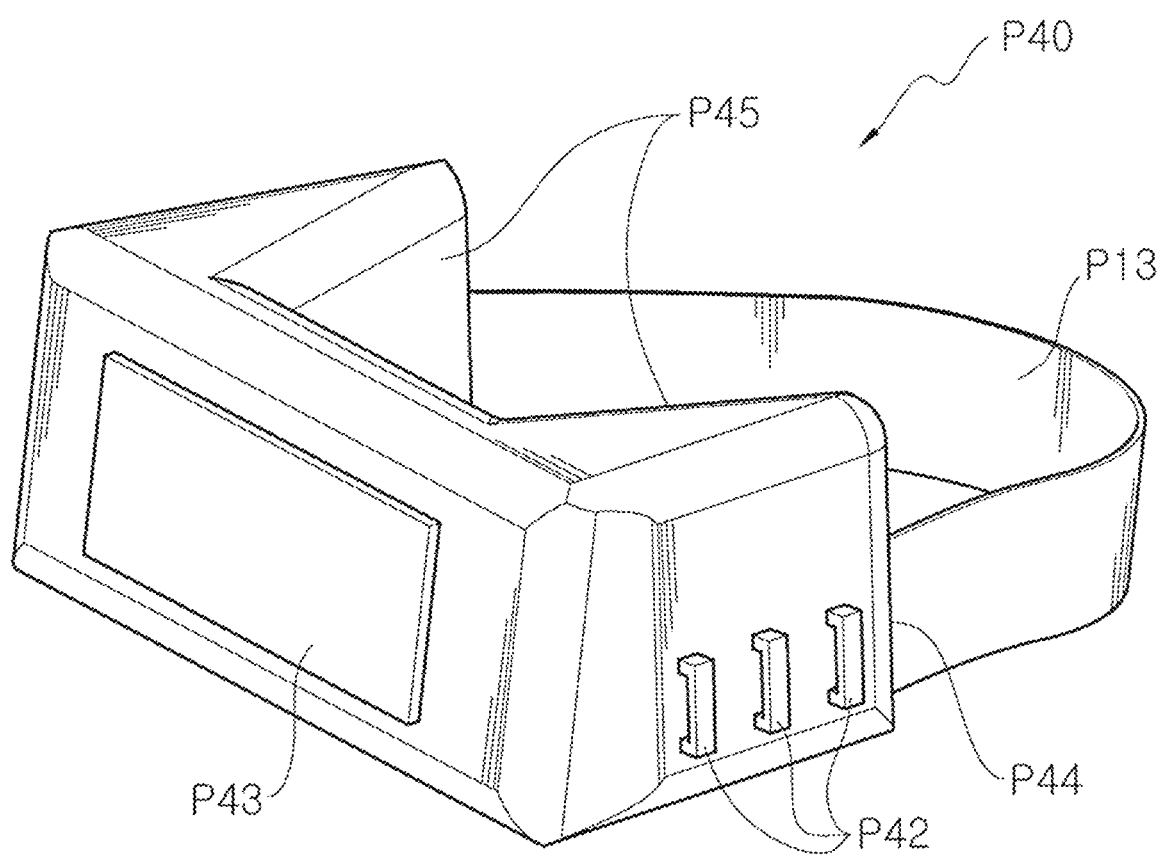
FIG. 8 is a perspective view schematically showing components of an affected upper limb exercise assistance apparatus according to the second embodiment of the present application.

FIG. 8 is a perspective view schematically showing components of an affected upper limb exercise assistance apparatus P40 according to the second embodiment of the present invention.

As shown in FIGS. 7 and 8, the affected upper limb exercise assistance apparatus P40 is coupled to both ends P44 of the waist support P13, so it may be held on the wearer's waist.

In detail, a curved groove is formed on a side of the affected upper limb exercise assistance apparatus so that it may be easily fitted to the wearer's waist, and a portion where the curved groove is formed is made by an elastic support P45 so that a shape of the affected upper limb exercise assistance apparatus may be easily deformed to be fitted to a waist shape of the wearer.

Further, as shown in FIG. 7, the affected arm mounting part P21 and the normal arm mounting part P31 are connected to each other at connection portions P22 and P32, respectively, through a belt P41. The belt P41 is disposed through a plurality of insertion holes P42 formed on a side of the body of the affected upper limb exercise assistance apparatus P40, whereby it is possible to guide movement of the belt P41 and prevent the belt P41 from sagging down due to its own weight.

Meanwhile, the affected upper limb exercise assistance apparatus P40 includes a first friction reduction pad P43 disposed on a side thereof facing the affected arm mounting part P21. The affected arm mounting part P21 also has a second friction reduction pad P23 disposed on a side thereof facing the wearer's waist.

Accordingly, friction between the affected arm mounting part P21 and the affected upper limb exercise assistance apparatus P40 may be reduced while the wearer's affected arm is moved, so it is possible to reduce resistance that interferes with movement of the affected arm mounting part P21 by the wearer.

In particular, the first friction reduction pad P43 and the second friction reduction pad P23 are made of Teflon, whereby friction can be minimized.

An inner side of the affected upper limb exercise assistance apparatus of the present invention may be made to be fitted to a curve of the wearer's waist, and an upper half of an upper side of the affected upper limb exercise assistance apparatus is narrow and made to have curved groove in comparison to a lower half of the upper side so that the upper side is fitted to a curve of an armpit of the wearer.

Figure 9:
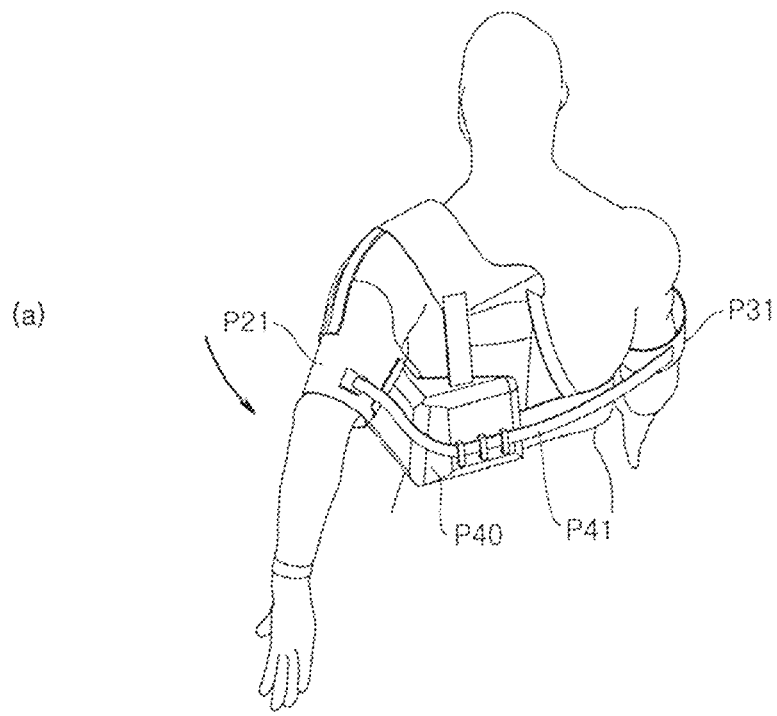
FIG. 9 is a view schematically showing movement of an affected arm and a normal arm of a user wearing the non-fixed shoulder brace according to the second embodiment of the present application.
Figure 9:
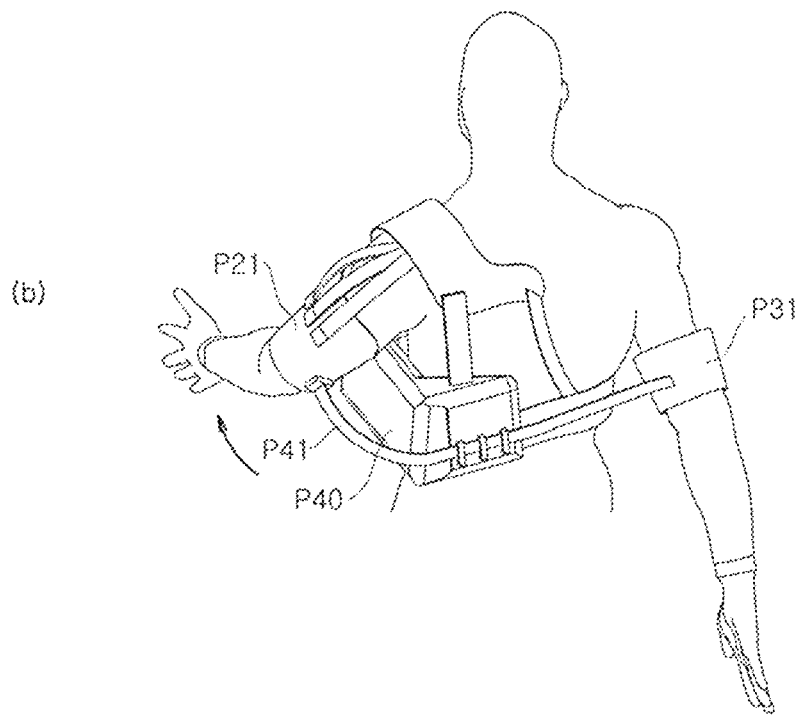
Figure 10:
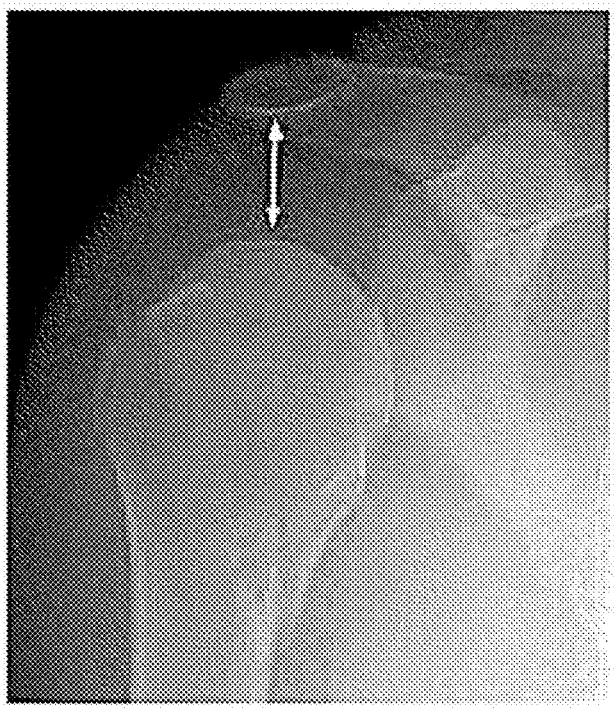
FIG. 10 is a picture and a view showing subluxation of a shoulder joint after cerebral apoplexy.
Figure 10:
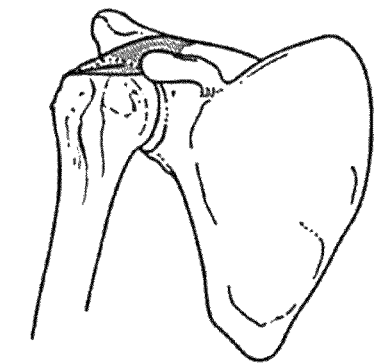
Figure 10:
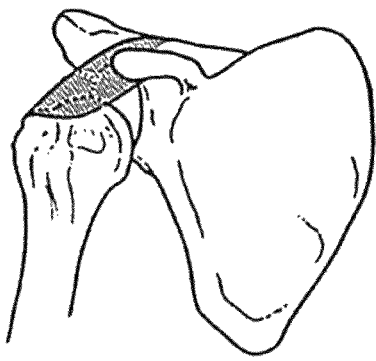
Figure 11:
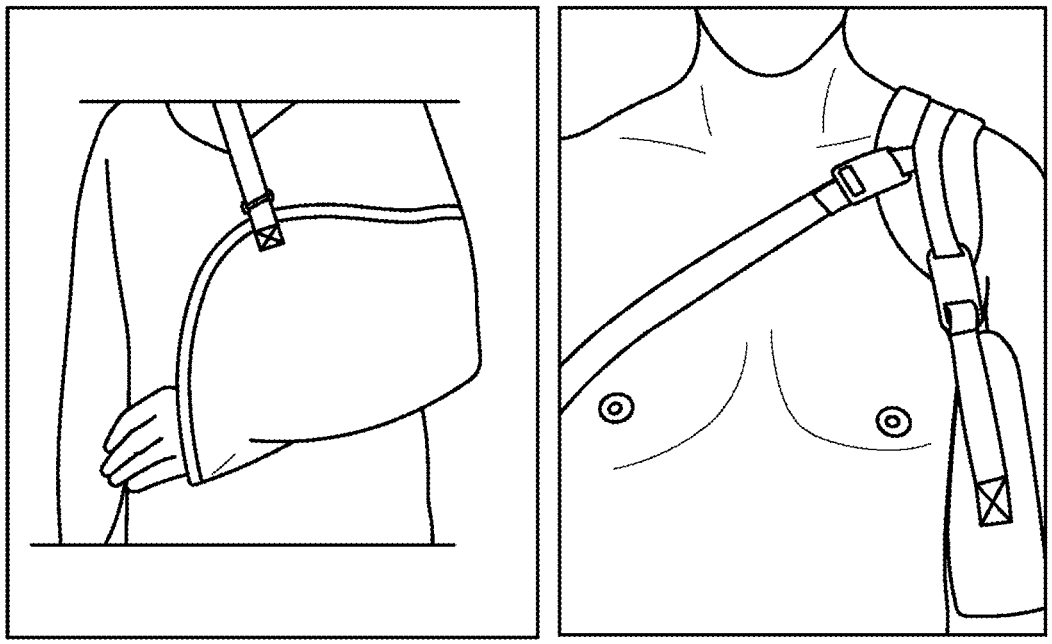
FIG. 11 is a picture showing a fixed-type shoulder brace for preventing subluxation of a shoulder joint.
Figure 12:
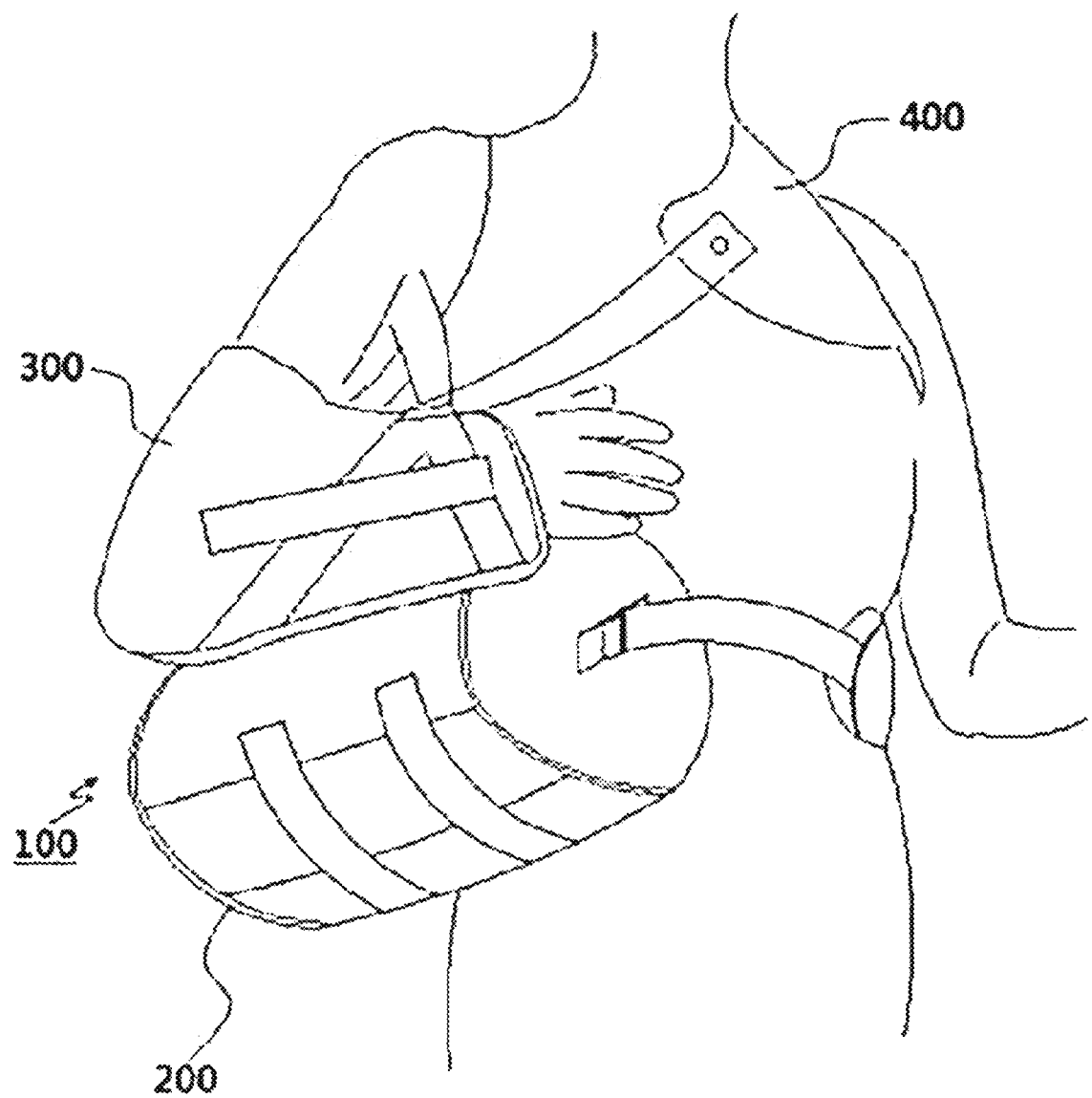
FIG. 12 is a view schematically showing a conventional fixed-type shoulder brace according to the prior art.

FIG. 9 is a view schematically showing movement of an affected arm and a normal arm of a user wearing the non-fixed shoulder brace P1 according to the second embodiment of the present application.

As described above, since the affected arm mounting part P21 and the normal arm mounting part P31 are connected to each other through the belt P41, movement of any one arm may assist movement of the other arm.

In detail, as shown in (a) of FIG. 9, when a wearer pivots forward a normal arm, the normal arm mounting part P31 is correspondingly moved forward. Since the affected arm mounting part P21 is connected to the normal arm mounting part P31 through the belt P41, the affected arm of the wearer is pivoted rearward in response to the movement of the normal arm mounting part P31.

Further, as shown in (b) of FIG. 9, when a wearer pivots forward an affected arm, the affected arm mounting part P21 is correspondingly moved forward. Since the normal arm mounting part P31 is connected to the affected arm mounting part P21 through the belt P41, the normal arm of the wearer is pivoted rearward in response to the movement of the affected arm mounting part P21.

Therefore, when the normal arm is moved forward and rearward in accordance with the wearer's walk, the affected arm may also be moved forward and rearward in response to the movement of the normal arm, so it is possible to prevent pain due to contracture of the affected shoulder joint and the elbow joint of the wearer.

Those skilled in the art may understand, with reference to be above description, that the present invention may be achieved in other embodied ways without a change of the spirit or the necessary features of the present invention.

Therefore, it should be understood that the embodiments described above are not limitative but only exemplary in all respects, the scope of the present invention is expressed by claims described below, not the detailed description, and it should be construed that all changes and modifications achieved from the meanings, the scope and equivalent concepts of the claims are included in the scope of the present invention.

The non-fixed shoulder brace according to exemplary embodiments of the present application may prevent subluxation of the affected shoulder joint while reducing contracture and pain by inducing movement of an affected arm through an affected upper limb exercise assistance apparatus.

The invention claimed is:

1. A non-fixed shoulder brace comprising:
   an affected shoulder support configured to be supported on an affected shoulder of a wearer;
   a waist support configured to be coupled to the wearer's waist;
   an affected arm mounting part configured to receive an arm of an affected upper limb of the wearer, and that is supported by an affected shoulder strap member from the affected shoulder support;
   a normal arm mounting part configured to receive an arm of the wearer's normal upper limb; and
   an affected upper limb exercise assistance apparatus coupled to both ends of the waist support and configured to be disposed between the wearer's waist and the affected arm mounting part,
   wherein the affected upper limb exercise assistance apparatus assists movement of the affected arm mounting part and comprises:
      a first cable connected to a front of the affected arm mounting part;
      a second cable connected to a rear of the affected arm mounting part;
      a motor unit having the first cable and the second cable wound thereon and being configured to tension the first cable and the second cable;
      a control unit configured to control a driving force and a rotation direction of the motor unit; and
      a power unit configured to supply power to the motor unit and the control unit; and
   wherein the normal arm mounting part includes a first inertia sensor, and
   the control unit is configured to extract a walk cycle of the wearer from a signal received from the first inertia sensor and is configured to correct the driving force and the rotation direction of the motor unit in accordance with the walk cycle.

2. The non-fixed shoulder brace of claim 1, wherein the affected upper limb exercise assistance apparatus comprises a first friction reduction pad disposed to face the affected arm mounting part, and
the affected arm mounting part comprises a second friction reduction pad disposed to face the wearer's waist.

3. The non-fixed shoulder brace of claim 2, wherein the first and second friction reduction pads are made of friction minimizing material.

4. The non-fixed shoulder brace of claim 1, wherein the affected arm mounting part comprises:
   a tension sensor and a second inertia sensor that is configured to measure a subluxation degree of the affected upper limb; and
   an electric stimulator that is configured to apply electrical stimulation to muscles of the affected upper limb according to the walk cycle of the wearer and the subluxation degree of the affected arm.

5. The non-fixed shoulder brace of claim 1, wherein the affected upper limb exercise assistance apparatus uses pneumatic artificial muscles.

6. The non-fixed shoulder brace of claim 1, wherein the waist support and the affected shoulder support are connected through a plurality of suspending shoulder strap members.

7. The non-fixed shoulder brace of claim 1, wherein the affected upper limb exercise assistance apparatus comprises an elastic support disposed to face the wearer's waist.

* * * * *